United States Patent [19]
Kirsner

[11] Patent Number: 5,916,173
[45] Date of Patent: Jun. 29, 1999

[54] METHODS AND APPARATUS FOR MONITORING FERTILITY STATUS IN THE MAMMALIAN VAGINA

[76] Inventor: Vaclav Kirsner, 2600 Brookwood Dr., Fort Collins, Colo. 80525

[21] Appl. No.: 08/806,921

[22] Filed: Feb. 26, 1997

[51] Int. Cl.⁶ .................................................. A61B 10/00
[52] U.S. Cl. ......................... 600/551; 600/591; 600/547; 600/587; 607/138
[58] Field of Search .................................. 600/551, 587, 600/591, 547, 372, 393; 607/138

[56] References Cited

U.S. PATENT DOCUMENTS

| | | | |
|---|---|---|---|
| 4,155,354 | 5/1979 | Rasmussen | 600/393 |
| 4,224,949 | 9/1980 | Scott et al. | 600/373 |
| 4,245,645 | 1/1981 | Arseneault et al. | 600/378 |
| 4,753,247 | 6/1988 | Kirsner | 600/547 |
| 5,215,090 | 6/1993 | Hon et al. | 600/376 |
| 5,240,010 | 8/1993 | Weinmann | 600/547 |
| 5,406,961 | 4/1995 | Artal | 600/591 |

OTHER PUBLICATIONS

William F. Ganong, M.D., Review of Medical Physiology 399–413 (Appleton & Lange 17th ed. 1995).

Ferin et al., The Menstrual Cycle Physiology, Reproductive Disorders and Infertility 3–113 (Oxford University Press 1993).

Kermit E. Krantz, The Anatomy and Physiology of the Vulva and Vagina and the Anatomy of the Urethra and Bladder, Scientific Foundation of Obstetrics and Gynaecology 47–64 (Elliot E. Phillip et al. eds. 1970).

D.M. Serr, The Uterus and Cervix, Scientific Foundation of Obstetrics and Gynaecology 65–80 (Elliot E. Phillip et al. eds. 1970).

Kermit E. Krantz, The Gross and Microscopic Anatomy of the Human Vagina, 83 Annals of the New York Academy of Sciences, Art. 2 at 89–104 (1959).

Charles Rose & Joseph T. Velardo, Histochemical Localization of Vaginal Oxidative Enzymes and Mucin in Rats Treated with Estradiol and Progesterone, 83 Annals of the New York Academy of Sciences, Art. 2 at 122–144 (1959).

Langdon Parsons et al., Abdominovaginal Electropotential Differences in the Menstrual Cycle, 83 Annals of the New York Academy of Sciences, Art. 2 at 237–244 (1959).

Carl G. Hartman, The Permeability of the Vaginal Mucosa, 83 Annals of the New York Academy of Sciences, Art. 2 at 318–327 (1959).

*Primary Examiner*—Richard J. Apley
*Assistant Examiner*—Justine R. Yu
*Attorney, Agent, or Firm*—Lee, Fishman & Isaac LLP; David J. Lee

[57] ABSTRACT

A method for monitoring fertility status in a female mammal comprising the steps of placing in the vagina of the female a probe having opposed electrodes, orienting the probe so that at least one of the electrodes is touching the cervix of the female, measuring across the electrodes at least one physical parameter indicative of the phase of the female fertility cycle, and comparing the value of the parameter with a reference; a probe useful in practicing this method comprises an elongated body having an insertion end, two electrodes attached to said body at the insertion end, and orienting means for orienting the body so that at least one of the electrodes touches the cervix of the female.

1 Claim, 9 Drawing Sheets

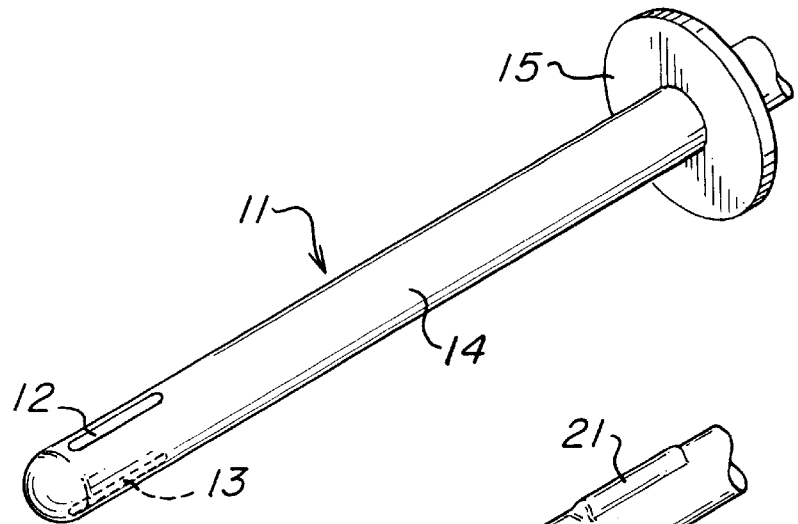
FIG. 1
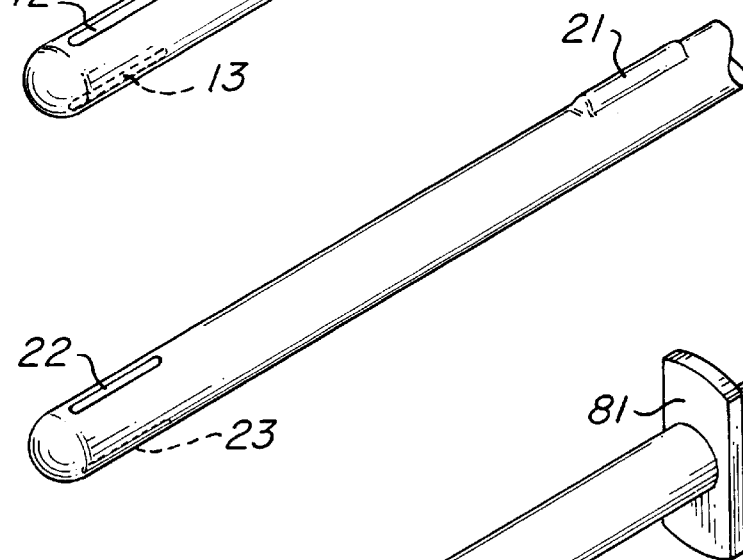
FIG. 2
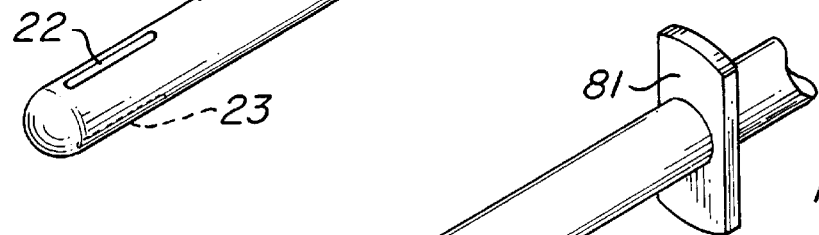
FIG. 8
FIG. 9
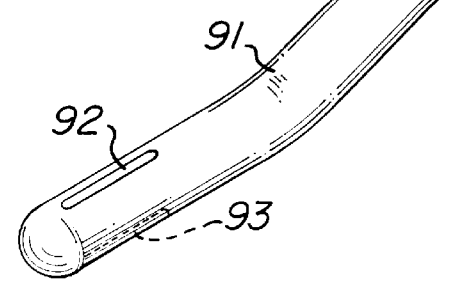

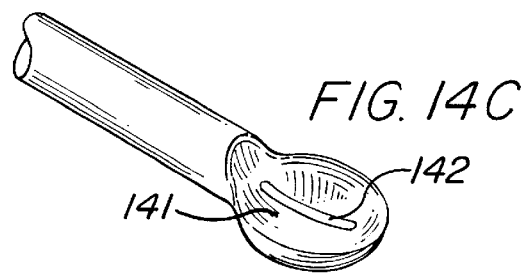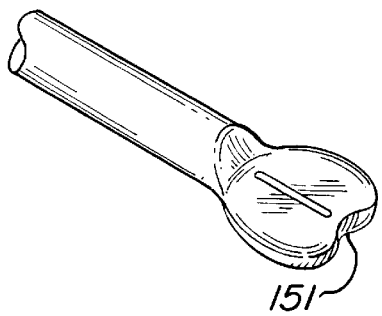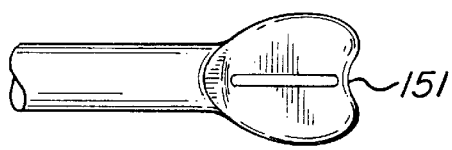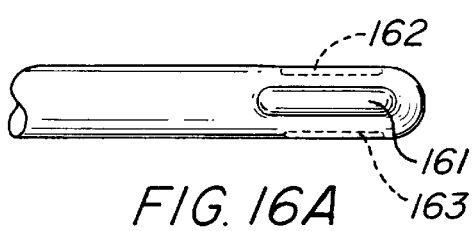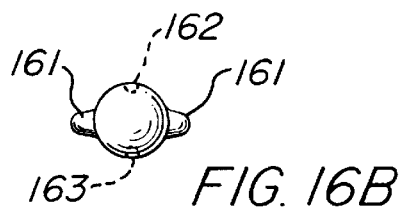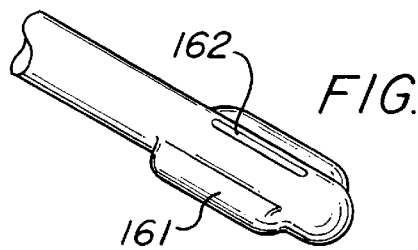

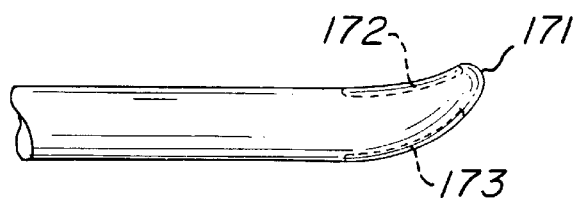
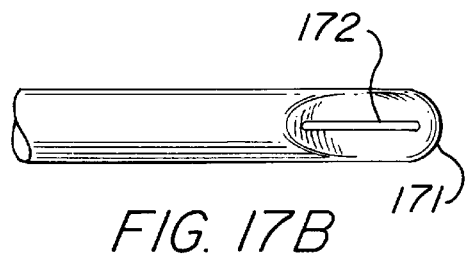
FIG. 17A  FIG. 17B
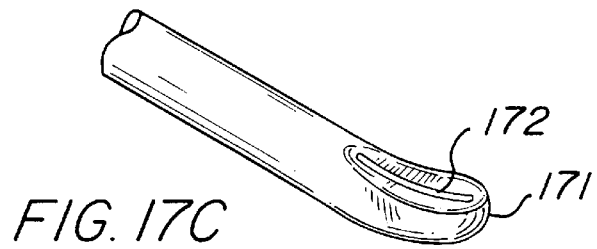
FIG. 17C

METHODS AND APPARATUS FOR MONITORING FERTILITY STATUS IN THE MAMMALIAN VAGINA

BACKGROUND OF THE INVENTION

1. Field of the Invention

The invention of this application pertains to the field of fertility monitoring. More particularly, the invention pertains to improved methods and apparatus for predicting and detecting ovulation in female mammals.

2. Description of the Related Art

Mammalian females become pregnant relatively rarely because they cannot conceive most of the time. Conception can occur only during a short period of several hours after the approximately once-monthly-produced egg becomes available for fertilization. In agricultural animals, such as cows, these cycles are shorter (approximately 3 weeks). In every case, unless the sperm reaches the egg at just the right time, fertilization and conception will not take place: the egg will deteriorate and be expelled. This occurs during menstrual bleeding in the human female.

Human conception is less than probable under the best of circumstances. A perfectly healthy young woman trying to become pregnant may go through three or four menstrual cycles before achieving pregnancy. The suspected reason for this is the relatively frequent failure of proper orchestration of the various hormonal stimuli and other processes that constitute the complex mechanism of menstrual cycle.

The process of the egg becoming available for fertilization involves the release of the egg ("ovum") from storage in the ovary. It is called ovulation. The process is under the control of a number of hormones released into blood circulation by glands in the brain as well as in the reproductive organs. The brain hormones, released by the pituitary gland, are the peptides luteinizing hormone and follicle stimulating hormone. The ovarian hormones are the steroids estrogen and progesterone. The varying levels of these hormones can be and have been measured in blood as well as in urine. Such varying levels of the sex hormones are called hormonal cyclic profiles because they describe endocrinologically the cycling of the female organism from the preparation of a new egg, through ovulation to its deterioration. A notable feature of the hormonal cyclic profiles is that they are rather flat in the preovulatory part of the cycle: no peaks appear there early enough, and so no useful warning of the forthcoming ovulation is provided by them.

For family planning or in animal husbandry, it is important to monitor the fertility status and its cyclical variations from infertile, through a few fertile hours, to infertile again. Determining the few fertile hours of the female is essential if pregnancy is desired, as is the case of the many infertile or subfertile couples desiring pregnancy but having difficulty achieving it. The same is of great economic significance to the agribusiness whose profitability depends on the efficiency with which it manages its a highly-priced individual animals, such as dairy or meat producing herds of animals to be bred at optimal time and minimal expense, whether using natural or artificial insemination in the process.

Fertility status monitoring is essential for family planning in the birth control sense, that is for the spacing of births or their complete prevention by the so-called natural family planning method (NFP). NFP is practiced in many parts of the world (such as among Catholic populations) even if the contraceptive pill has had a significant impact on the birth control practice in the United States and other industrial and developed countries. Health awareness including concerns about side effects of medications, about interfering with one's hormonal biochemistry and related issues mean that modern women may well be receptive to scientific family planning, that is fertility awareness assisted by a reliable scientific technique.

Over the years, a number of different approaches to fertility monitoring have been undertaken. The oldest is the basal body temperature method. This is no longer favored by the gynecological profession. Fertility specialists are now more in favor of endocrinology-based methods of ovulation detection.

Urinalysis Chemical Kits

The ovulation detection market, comprised primarily of women with infertility problems, is being served primarily by chemical kits. The kits are small chemical test strips or test tubes that are used at home to self-analyze the woman's urine samples during the several days that the woman estimates may include ovulation. The kits are sold over the counter through pharmacies, supermarkets, and discount chains as well as by some doctors directly to their patients. Some of the brands included in this group are First Response (Tambrands), Q-Test, OvuKit, OvuStick, and OvuQuick (Quidel Corporation), Right Moment (Seragen Diagnostics Inc.), and Discretest (Chefaro Proprietaries Ltd.)

The kits are designed to detect the luteinizing hormone (LH) surge which accompanies ovulation. The LH surge shows up in urine after it occurs in blood, and it occurs in blood within 12 to perhaps 36 hours of ovulation. The user takes a urine sample once or twice a day and places a chemical in it, looking for a color change.

However, women with infertility problems, who are the main customers for these products and who may be treated with Clomiphene, an ovulation induction drug, cannot rely on the chemical kits because of false positive indications. The chemical kits do not detect premature ovulation, and women being treated with Perganol, another ovulation inducer, may ovulate prematurely and waste the cost of the Perganol treatment (about $750 per cycle).

Doctors nevertheless use the kits to time patient office visits for advanced reproductive procedures including more rigorous analytical tests. The rigorous and costly tests which the doctors may employ are lab measurements of sex hormone concentrations in blood, and ultrasound imaging of the ovaries and uterus. Ultrasound shows the rupturing of the follicle required for the release of the egg, the egg becoming available for fertilization: this egg release (ovulation) occurs with approximately 80% of ruptured follicles.

The chemical urinalysis kits are based on a simplified version of the immunochemical analytical method for body fluid analysis, taking advantage of the analytical sensitivity and specificity of the monoclonal antibody reaction with the luteinizing hormone (LH). Several problems are inherent in the kits:

Urine is used as the body fluid rather than blood plasma. While not as uncomfortable as blood sampling, urine sampling is not a particularly clean or pleasant procedure. Detecting the LH surge in urine is an indirect measurement of the LH surge in the blood, which is the operative hormonal signal involved in ovulation. The LH surge in urine reflects the clearance of LH from blood and, as such, is delayed and diluted. Spurious LH surges occur.

The rigor of the original laboratory procedure is sacrificed to simplicity and ease of use in the home environment; yet the procedure is still tedious. And, the LH surge may be missed because it often occurs overnight and lasts only a few hours. This is why some women may use two kits per cycle, one in the morning and one in the evening.

These kits have no true predictive capability, and are thus inapplicable for birth control purposes. These kits are unsuitable for interfacing with a physician's instrumentation or computer. These kits are subject to shelf-life limitations.

Personal Contraceptive System

In The importance of the ovulation-predictive capability is reflected in U.S. Pat. No. 5,467,778 (Catt et al., Nov. 21, 1995) assigned to Unilever Patent Holdlings B. V. of Netherlands. The method of this patent is implemented in the "Personal Contraceptive System" of Unipath Ltd. It consists of detecting, in a woman's urine, a metabolite of estrogen which anticipates by about one day the luteinizing hormone that peaks about 12 hours before ovulation. Since the supply of reagents is limited to about five days, the user needs to estimate on which day of her menstrual cycle she should start using the system. She does that based on her history of menstrual cycles. Because of variable lengths of successive cycles in most women, this represents a disadvantage.

The "Personal Contraceptive System" of Unipath Ltd. is an attempt at an improvement upon certain inadequate features of the commercially available luteinizing hormone (LH) kits. Two significant improvements have been introduced: i) the addition of an estrogen metabolite to the diagnostic measurement, and ii) the measurement is performed instrumentally rather than as a subjective judgment of a color change by the woman user.

The urinary concentration of the estrogen metabolite E3G peaks only within 24 hours prior to the LH surge. This is not early enough to serve as a marker of the beginning of the fertile phase. Their literature states that "a sustained rise in E3G can be used to identify the start of the fertile phase". They claim that this has been achieved successfully in 78% of tested menstrual cycles based on 131 women, 557 menstrual cycles.

While the Unipath "Personal Contraceptive System" has been introduced to the market in Britain, the testing for its statistical reliability is still in progress. The use by Unipath Ltd. of the hormone concentrations to define the fertile period is an inherently unreliable approach because the hormones are merely the input signals into the physiological mechanism of fertility status. Even more inherently unreliable is the use of an ill-defined rise as opposed to a peak in the measured estrogen metabolite.

Microprocessor-Controlled Thermometers

The advent of microprocessor electronics antedated the replacement of the radioimmunoassay by non-radioactive immunoanalytical procedures that only later could lend themselves for adaptation into the home-use analytical kits discussed above. Since the late sixties, the microprocessor technology has been applied by a number of people to the well-tried basal body temperature approach to family planning.

One of the most publicized of the microprocessor-controlled thermometers is the Swiss-made Bioself which has an almost 30 year long history. As an example, in a 1989 publication in Fertility and Sterility (The American Fertility Society), the company and its consultants claimed that the Bioself 110 "identified the 6-day fertile period in 86.4% of 220 cycles studied and 5 days in 93.2% . . . On average, the device identified 10.9 fertile days and 10.6 post-ovulatory "safe" days per cycle."

Another computerized thermometer product is the U.S.-made Rabbit Ovulation Computer. Their advertising literature claims that the device is "used by gynecologists" and that "a woman's fertile period . . . lasts for approximately 72 hours." Some other similar U.S.-made products are Cycle-Logic and Women's Biomonitor. There is also a Japanese-made L-Sophia, marketed in Japan.

Two chief improvements over ordinary mercury thermometers are achieved with the microprocessor electronics: a) several months of data can be stored in the memory, and b) datasmoothing to minimize the effects of random noise for which the temperature measurements are notorious.

These products are not recognized as medically valid by the gynecological community, although they may be acceptable to some of the older generation of family and general practitioners and gynecologists. This is because no amount of data smoothing by the microprocessor can cancel the well understood fact that the so-called basal body temperature (BBT) is a secondary parameter that reflects, among other things, progesterone rise in blood after ovulation. Even though in some women in some cycles a dip in the temperature may be observed before the post-ovulatory temperature rise, the general prevailing view of the BBT method is that it is of little value due to its lack of predictive capability and due to its fundamental unreliability. The devices tend to be cumbersome to use and expensive.

Combined Vaginal and Oral Resistivity Detector

Another electronic ovulation detector offered to the market was the Cue detector from Zetek. It consisted of two resistivity sensors: one oral (to detect a change in resistivity of saliva in the mouth 5 or 6 days before ovulation), and one vaginal (to detect a change in resistivity of the mucus in the vagina, marking ovulation). The Cue monitor measured the concentration of electrolytes, particularly common salt, in the saliva and in vaginal mucus. These are, at best, remote indicators of the physiological changes that characterize the fertility status of the cervical uterine tissues. In addition, the Cue monitor was cumbersome to use, expensive, and not at all feminine in any sense. It was considered unreliable and too expensive.

The Cue Monitor from ZETEK is but one example of a number of conductometric impedance or resistance meters known in the prior art. Additional examples may be found in my 1988 U.S. Pat. No. 4,763,247 which is discussed below. We first reference here a more recent (1993) patent by Weinmann.

Weinmann Patent

Similar to the ZETEK Cue Monitor, the apparatus disclosed in U.S. Pat. No. 5,240,010 (Weinmann, Aug. 31, 1993) sends a high frequency AC current through two metal electrodes into the vagina and measures the voltage drop across the electrodes, to monitor changes in cervical mucus secretions via their effects on the "polarization impedance of the metal electrode/cervical mucus interfaces" placed "near the entrance of the cervix." The reported menstrual cyclic pattern is the same as in other conductometric prior art: it shows a midcycle minimum (dip) between approximately identical levels of higher impedance. This is expected because of the known increase at midcycle of water and electrolyte content in the mucus.

Kirsner Patent

U.S. Pat. 4,763,247 (Kirsner, Jun. 28, 1988) applies to non-metallic electrodes a time-varying voltage of low amplitude (50–500 mv) and high frequency to monitor redox activity in the vagina, desirably at a position such that the electrodes may contact the posterior fornix. For best results, the electrodes should be located in that region. The reference discloses that the size and location of the electrodes may have a significant effect on the response.

This patent discloses an indication of the onset of ovulation which is predicted by a peak that precedes the ovulation marker. The ovulation marker is a dip (minimum) in the profile, usually the lowest value in the cyclic pattern. It tends to a given numerical value at a given calibration. The ovulation-predictive peak signal is not yielded by the Weinmann patent nor by any other electrometric fertility monitoring apparatus. Yet, ovulation-predictive capability is crucial for a scientific family planning tool.

The Kirsner technique uses the cervix as a monitor of the proper functioning of the developing follicle, as it is preparing the entire reproductive system for ovulation. The Kirsner technology detects the adequacy of the hormonal effects, or their inadequacy, as the case may be.

The Kirsner technique detects all the cyclic events that lead to (i.e., anticipate) ovulation. First, the selection of the dominant follicle is detected around day 7 of the menstrual cycle, and the interval of dominance is monitored via easily measured features in the cyclic profile. Then the oocyte's readiness for ovulation is signaled. This is followed by the ovulation marker caused probably by the rapidly increased progesterone which is released by the luteinized granulosa cells. A number of post-ovulatory peaks in the cyclic profile will also be diagnostically useful.

SUMMARY OF THE INVENTION

One object of the inventions of this application is to improve the sensitivity and signal-to-noise characteristics of prior methods and apparatus for monitoring fertility in female mammals. Another object of the inventions is to increase the reliability and repeatability of fertility monitoring in female mammals. Another object of the inventions is to configure a vaginal fertility probe that, upon insertion, lodges itself in such a manner that at least one electrode of the probe is in contact with the cervix, and more preferably in such a manner that the other electrode of the probe is in contact with the posterior fornix. A final object of the inventions is to configure a vaginal probe that is comfortable to the user upon insertion in the vagina for taking a diagnostic measurement.

One invention of this application comprises an improved method for monitoring fertility in female mammals. The method, in particular, involves the steps of placing in the vagina of the female a probe having two electrodes, orienting the probe so that at least one of the electrodes makes contact with the cervix of the female, measuring across the electrodes at least one physical parameter indicative of the phase of the female fertility cycle, and comparing the value of the parameter with a reference value. Preferred embodiments of this method include placing one electrode in contact with the cervix and the other electrode in contact with the posterior fornix, use of non-metallic electrodes, and measurement of admittance or alternating current across the electrodes.

Another invention of this application further comprises an improved apparatus for predicting and detecting ovulation in female mammals. The apparatus, in particular, is a vaginal probe comprising an elongated body having an insertion end, a back end, and a central section having a rounded cross-section, two electrodes attached to the body at its insertion end, and orienting means for orienting the body so that at least one of the electrodes makes contact with the cervix of the female. Preferred embodiments of this apparatus use non-metallic electrodes and are configured so that the orienting means orient the body so that one electrode makes contact with the cervix of the the female and the other electrode makes contact with the posterior fornix of the female, typically by having the electrodes attached to the probe body on opposite sides of its insertion end.

Preferred orientation means include indicator means attached to or protruding from the probe body, bends in the probe body, or modifications to the insertion end of the probe body. Preferred modifications include providing a flat or concavity at the insertion end that bears one of the electrodes. The flat or concavity can be enlarged relative to the rest of the probe body. Alternatively, the insertion end can be provided with elongated protrusions between the electrodes, the axis of elongation corresponding with the axis of the insertion end.

These preferred orientation means can be combined. For example, the body of a probe having elongated protrusions at the insertion end can be bent at the junction between the insertion end and the remainder of the probe body. Generally speaking, the orientation means enhance the comfort of the probe to the female when used to measure conditions in the vagina.

BRIEF DESCRIPTION OF THE DRAWINGS

FIG. 1 depicts a fertility probe of the prior art.

FIG. 2 depicts a fertility probe of the invention having indicator means for positioning the probe in the vagina so that one electrode contacts the cervix.

FIG. 8 depicts another embodiment of a fertility probe of the invention having indicator means for positioning the probe in the vagina so that one electrode contacts the cervix.

FIG. 9 depicts an embodiment of a fertility probe of the invention having a bend in the probe body for positioning the probe in the vagina so that one electrode contacts the cervix.

FIGS. 14A through 14C depict an embodiment of a fertility probe of the invention having an electrode-bearing concavity at the insertion end of the probe body that extends outwardly beyond the remainder of the probe body.

FIGS. 15A through 15D depict another embodiment of a fertility probe of the invention having an electrode-bearing flat portion at the insertion end of the probe body that extends outwardly beyond the remainder of the probe body.

FIGS. 16A through 16C depict an embodiment of a fertility probe of the invention having two elongated protrusions extending from the insertion end of the probe between the electrodes, the axis of elongation corresponding substantially to the axis of said insertion end.

FIGS. 17A through 17C depict an embodiment of a fertility probe of the invention having both a bend in the probe body and an electrode-bearing concavity at the insertion end of the probe body.

DESCRIPTION OF THE PREFERRED EMBODIMENTS

Figure 3A:
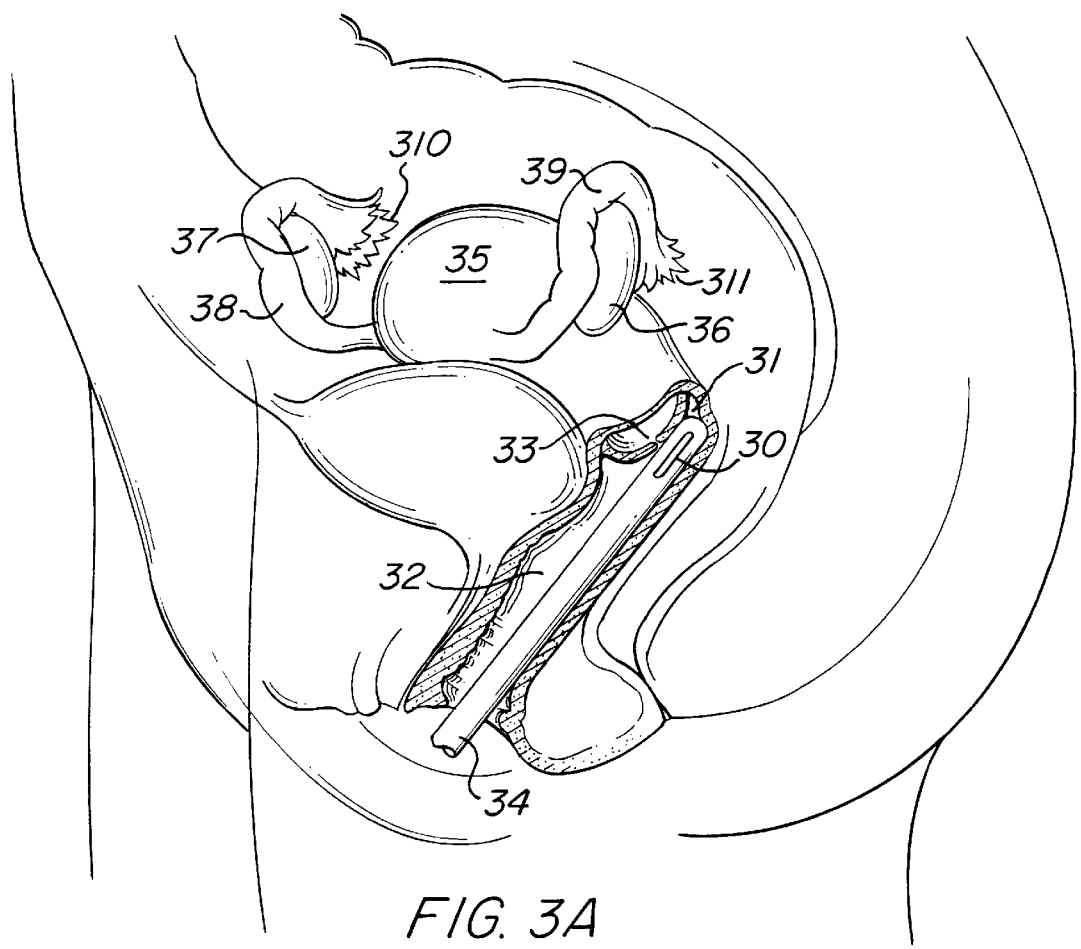
FIGS. 3A and 3B depict the fertility probe of FIG. 2 inserted in the vagina of a human female in two different electrode-orientation positions.

Referring now to the drawings in detail, FIG. 1 shows a fertility probe of the prior art. In particular it shows the probe of FIG. 2 of my U.S. Pat. No. 4,753,247. The probe 11 comprises a rigid or semi-rigid cylindrical body 14 (approximately 10 cms in length and 1 cm in diameter for human use) having a rounded distal or insertion end insertable into the vagina, with the insertion end extending into the region of the posterior fornix. Two non-metallic electrodes or elements 12 and 13 are attached to probe body 14. The electrodes 12 and 13 can be of any shape and size within reason. The attachment of electrodes 12 and 13 to body 14 can be accomplished by any method known for attaching an electrode to a substrate, including but not limited to gluing, bonding and embedding.

The proximal end element 15 of probe 11 is circular and featureless. There is no guide to orient probe 11 during and after the process of insertion into the vagina. The electrode positioning with respect to the cervix was indeterminate. The importance of having at least one electrode in contact with the cervix of the female was not recognized.

FIG. 2 depicts a probe of the invention which makes it possible to control the orientation of the sensor so that one of its electrodes makes contact with the cervix itself. The probe has electrodes 22 and 23 disposed opposite one another at the insertion end of the probe. Indicator means in the form of an elongated protrusion 21 are lined up with electrode 22. Protrusion means 21 give the user a definite guide to orient the probe during and after the process of insertion into the vagina.

Figure 3B:
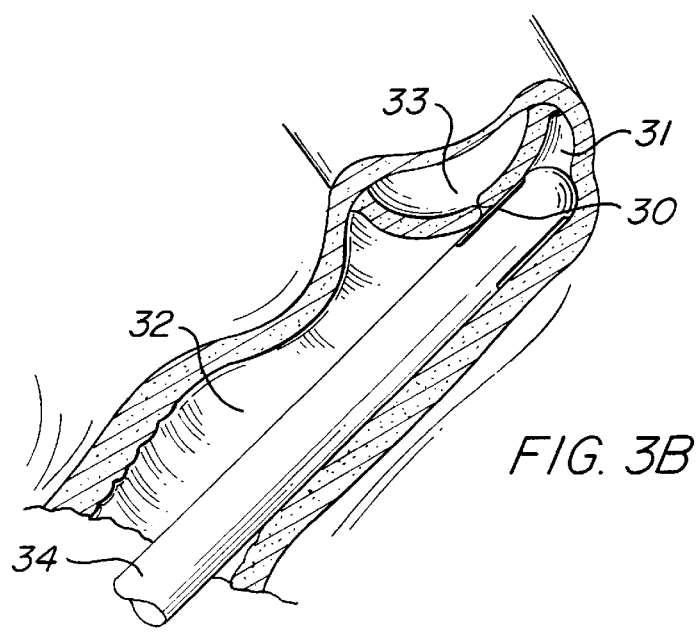

This can be understood with the help of FIGS. 3A and 3B, which show the anatomical arrangement of a standing woman in a side view. FIGS. 3A and 3B show the posterior fornix region 31 at the upper end of the vaginal canal 32 into which extends the semispherical protrusion of the cervix 33.

FIG. 3A depicts additional details of the anatomical arrangement of the reproductive system, including the body of the uterus 35 (from which the cervix 33 protrudes downward into the vagina 32), and including also the left and right ovaries 36 and 37 and left and right oviducts (Fallopian tubes) 38 and 39 that grow from the respective sides of the uterus 35, curving around the ovaries and ending in the funnel-like arrangements of the fimbria 310 and 311. The purpose of the fimbria 310 and 311 is to capture the egg when it ovulates by bursting out of one or the other ovary 36 or 37 at the time of ovulation to travel through the respective oviduct toward the uterus (fertilization would occur in the oviduct if sperm have been injected and traveled effectively through the cervix and uterus.)

FIG. 3A shows a probe 34 inserted so that neither of the electrodes, one of which is seen as electrode 30, is in contact with the cervix. FIG. 3B shows the probe 34 in a different orientation, with electrode 30 touching the cervix 33. This position leads to superior diagnostic results.

The probe 34 is inserted in the same manner as a vaginal tampon, and will naturally go as far as the posterior fornix region 31, at the far upper end of the vaginal canal 32, in the neighborhood of the protruding cervix 33. Without the guiding means such as provided by the protrusion 21 in FIG. 2, the electrode contact location is indeterminate. With the two electrodes on the opposite sides of the shaft, they can both be oriented away from the cervix, both making contact instead with the posterior fornix region.

This posterior fornix region 31 is sometimes referred to as the transition region. It comprises a mixture of epithelial cells of both the cervix type and the vaginal wall type. Those two types have different biological properties, including different sensitivities to the steroid hormones as evidenced by the results discussed below (in particular, in relation to FIGS. 5, 6, and 7). With the facility of guiding means such as provided by the protrusion 21 in FIG. 2, the insertion can be made with the electrode (electrode 22 in FIG. 2, electrode 30 in FIG. 3B) in the upper position rather than to the side: this brings the electrode into the desired contact with the cervix 33. Only the other electrode (electrode 22 in FIG. 2) will now be touching the wall epithelium, in posterior fornix region 31.

Figure 4:
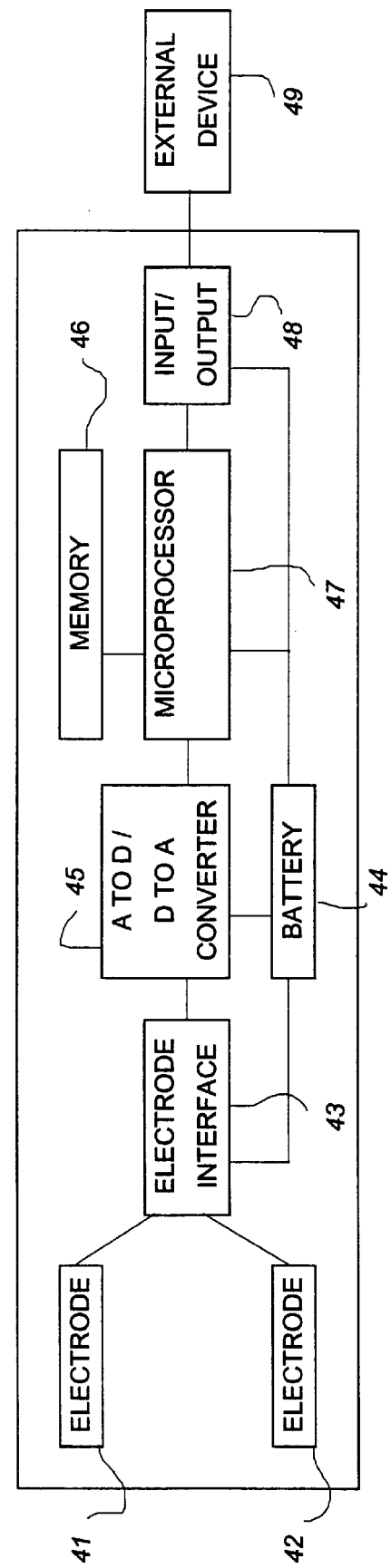
FIG. 4 is a block diagram of the electronic components of the fertility probe of FIG. 2.

FIG. 4 is a block diagram of the electronic configuration of the probe of the invention. It represents a digital electronic implementation of the design discussed in my U.S. Pat. No. 4,753,247 with the added benefits of memory and external interface. Microprocessor 47 generates the waveform used in the probe measurement. The digitally generated waveform is converted into an analog signal in converter 45 and applied to the electrodes 41 and 42 via electrode interface conditioning electronics 43. The electrode response is similarly converted into digital data by converter 45 for processing by microprocessor 47. The processed data is displayed on LCD or LED display (not shown) and stored in memory 46 for optional downloading at a later date via input/output interface 48 to external device 49, which can be a computer, for example.

Figure 5:
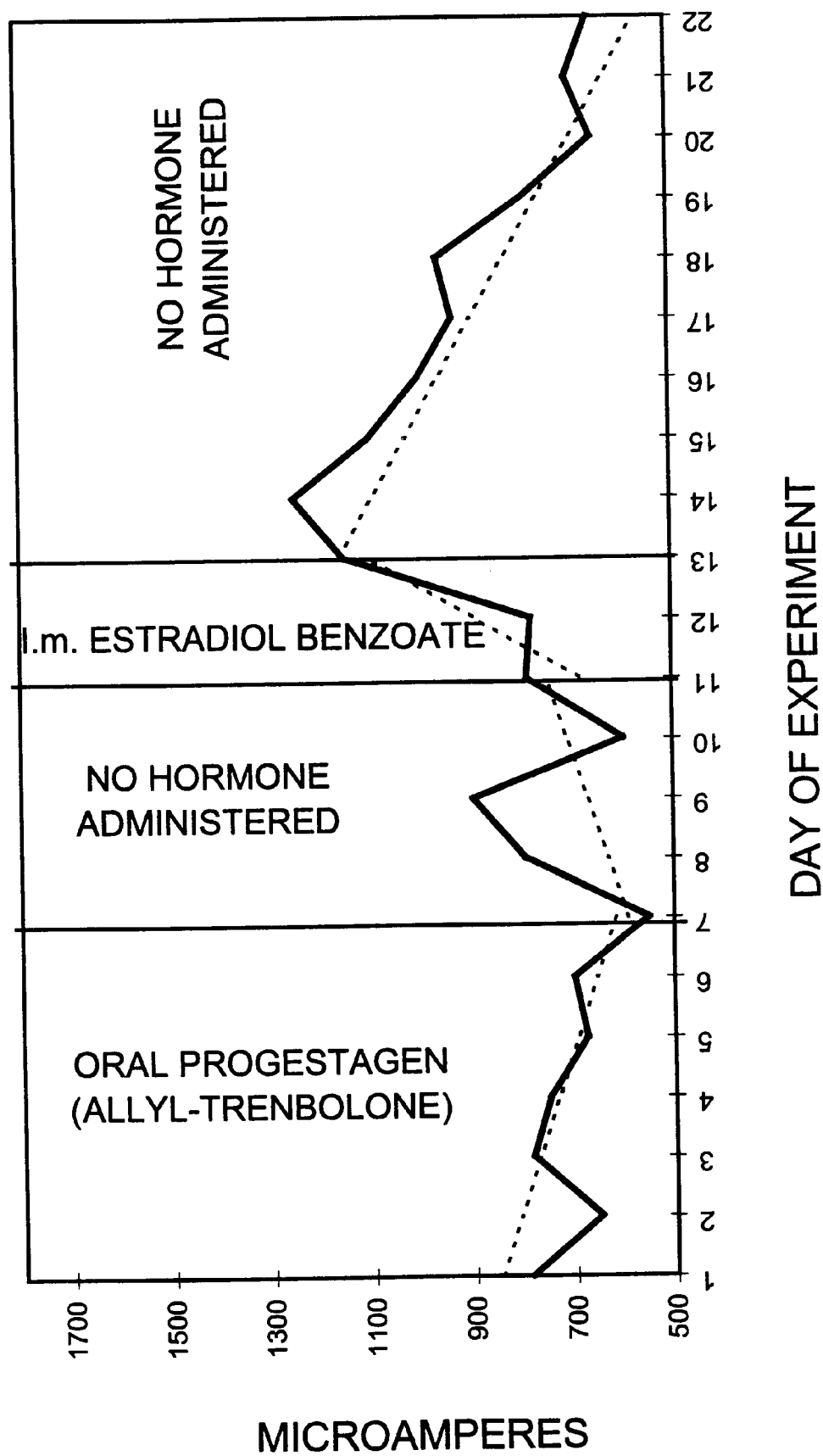
FIG. 5 is a graph of the fertility probe response to the administration of progesterone and of estrogen in an ovariectomized female pig.

FIG. 5 is a graph of the probe response to the administration of progesterone and of estrogen in an ovariectomized female pig, that is a pig whose ovaries have been removed so that the animal is not producing the steroid sex hormones estrogen and progesterone. The experiment showed that orally administered progesterone (P4) caused a decrease of the signal. Upon discontinuation of P4, the signal returned toward the initial level at about the same rate. Estrogen (E2), at a two orders of magnitude lower dose via an intramuscular injection, caused a significantly higher increase of the signal. Upon discontinuation of E2, the signal decreased and the rate of this change was again greater than the response to progesterone. The results are consistent with the features of the cyclic profiles in all three mammalian species (human, bovine and porcine) studied with the technology to date, and with the postulated mode of operation: the tissue of the cervix uteri responds to the steroid hormones as the hormones are brought to the tissue by circulation and the probe registers these responses.

The steroid hormone effect experiment was performed as follows: Three pubertal gilts were surgically ovariectomized (OVX). After recovery from surgery, probe readings were taken during daily feeding in individual feeders. Over the first seven days, gilts were treated with the oral progestagen, allyl-trenbolone (Regumate, Roussel-UCLAF plc) administered at a dose of 20 mg per day in oil as a top dressing on sow nuts. After a four day withdrawal period, gilts received intramuscular injections of estradiol benzoate in oil as follows: 250 ug at 11 AM and 9 PM on day 12 and 500 ug at 11 AM on day 13 of the experiment. Probe readings were taken daily to day 22. Successful recordings were only achieved in one of the OVX gilts due to problems with effective probe insertion in these immature, postoperation steroid-deficient animals. The data for this animal are shown in FIG. 5.

Following are data derived using a vaginal probe in two positions in a human female. One position made contact with the cervix and the other position had the electrodes oriented 90 degrees away from the first position, as discussed in onnection with FIGS. 3A and 3B above.

| Day | Cervix | Posterior Fornix | Ratio E/P |
| --- | --- | --- | --- |
| 7 | 176 | 136 | 1.29 |
| 8 | 142 | 133 | 1.07 |
| 9 | 200 | 161 | 1.24 |
| 10 | 212 | 170 | 1.25 |
| 11 | 230 | 169 | 1.36 |
| 12 | 196 | 146 | 1.34 |
| 13 | | | |
| 14 | 187 | 143 | 1.31 |
| 15 | 213 | 178 | 1.20 |
| 16 | | | |
| 17 | 187 | 143 | 1.31 |
| 18 | | | |
| 19 | 185 | 148 | 1.25 |
| 20 | 186 | 152 | 1.22 |
| 21 | 184 | 154 | 1.19 |
| 22 | | | |
| 23 | 198 | 177 | 1.12 |

Figure 6:
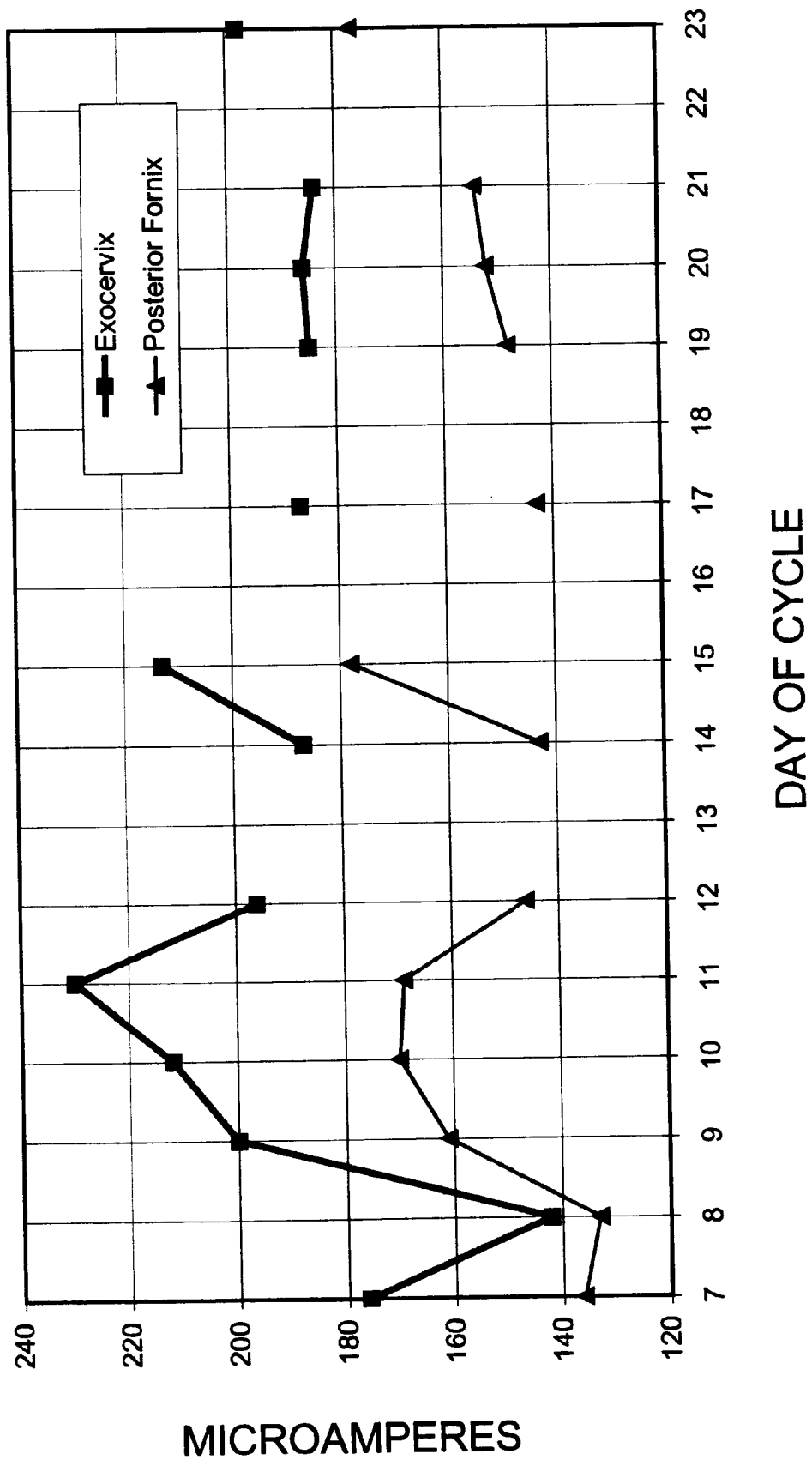
FIG. 6 is a graph comparing fertility probe readings with electrode contacts in two different positions in a human female.
Figure 7:
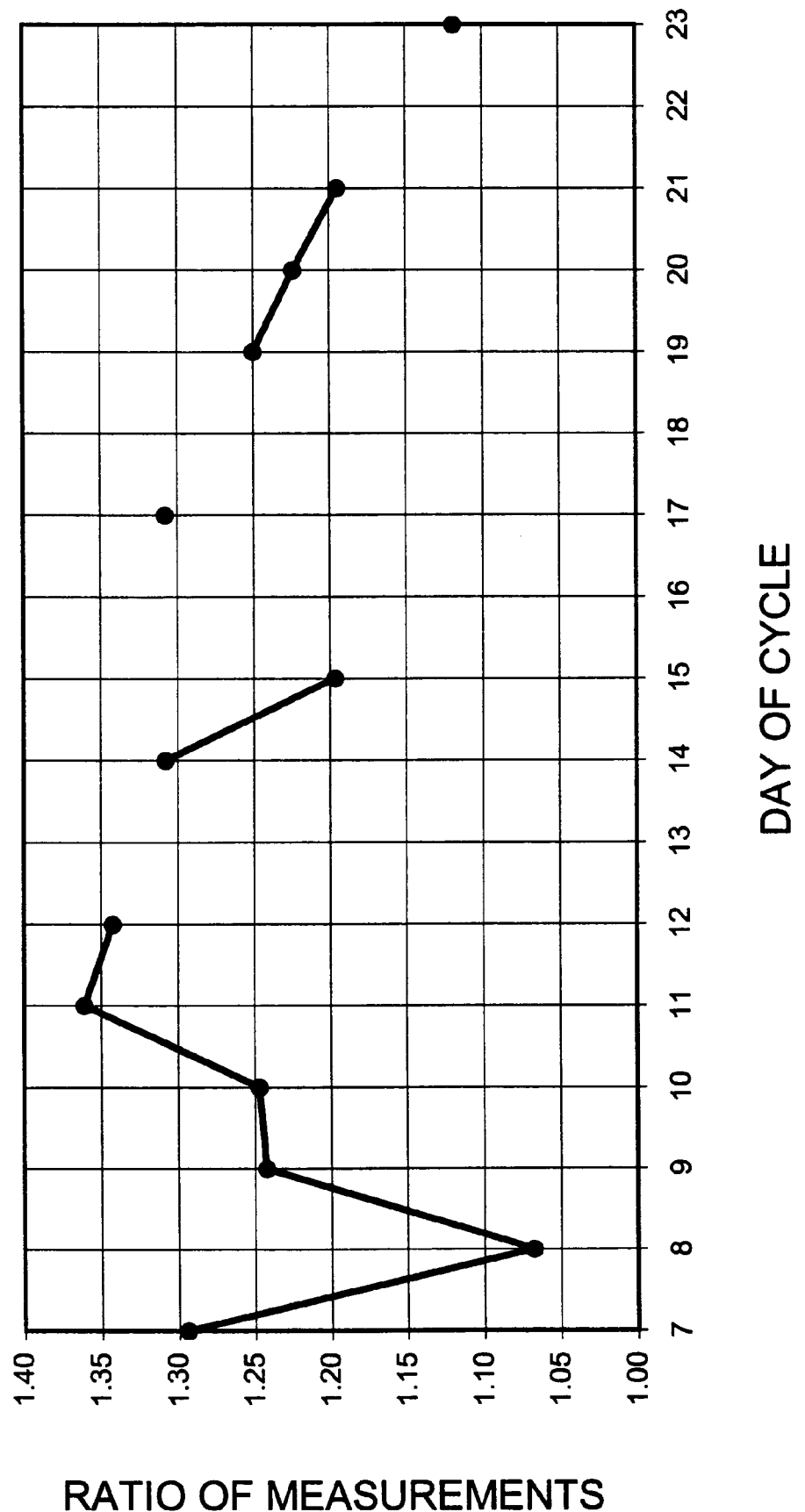
FIG. 7 is a graph of the improvement ratios for the fertility probe readings of FIG.6.

These data are plotted in FIGS. 6 and 7.

Noteworthy features of FIG. 6 include the fact that all the values of measurement taken with the electrodes in the cervix orientation (with electrodes oriented top to bottom) lie well above those taken with the electrodes in the posterior fornix (side to side) position. The ratio of the improvement in the signal is represented in FIG. 7, which shows the improvement to be mostly between 20% and 40%. The other important feature is that the improvement is particularly pronounced in the first half of the menstrual cycle. That is the predictive part where the signal to noise aspect matters the most.

The gaps in the data are due to the fact that on those days (13, 16, 18 and 22) the woman volunteer did not record any measurements. This does not detract from the fact that, consistently throughout the test, the cervix-to-electrode contact is superior to the posterior fornix contact. It is imperative to control the electrode orientation in the described sense also for the reason that the above data show that, without such control, up to 40% uncertainty would be introduced into the measurement result. The extent of such measurement error would vary from day to day, being most significant and most variable in the most critical part of the menstrual cycle, before ovulation.

A number of examples of other ways in which to achieve the desired probe orientation are shown in FIGS. 8 through 17. FIG. 8 depicts another embodiment of a fertility probe of the invention having indicator means for positioning the probe in the vagina so that one electrode contacts the cervix. End-wing cross-member 81 serves to guide the proper electrode orientation depicted in FIG. 8. The wings are on the same sides of the body of the probe as the electrodes 82 and 83 that are located at the other end of the shaft.

Another way of facilitating correct electrode positioning is to introduce one or more bends in the body of the probe. FIG. 9 depicts an embodiment of a fertility probe of the invention having a bend in the probe body for positioning the probe in the vagina so that one electrode contacts the cervix. This altered longitudinal shape of the shaft of the probe takes advantage of the mild s-shaped curvature of the vaginal canal. FIG. 9 depicts a probe with an upward bend 91 of the probe shaft, with the two electrodes 92 and 93 in the plane of the bend.

Figure 10:
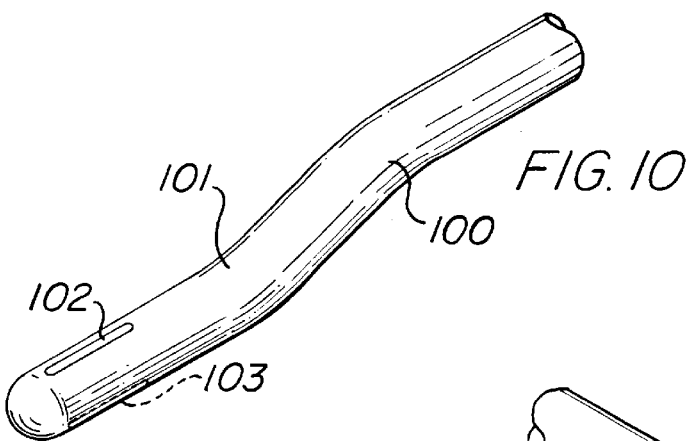
FIG. 10 depicts an embodiment of a fertility probe of the invention having a bend in the probe body for positioning the probe in the vagina so that one electrode contacts the cervix.

The probe of FIG. 10 takes the approach of FIG. 9 a step further. FIG. 10 depicts an embodiment of a fertility probe of the invention having two bends in the probe body for positioning the probe in the vagina so that one electrode contacts the cervix. As with the probe of FIG. 9, the positioning is accomplished automatically by virtue of the mildly curved vaginal canal (as seen in FIGS. 3A and 3B). The double or S-bend in the body shaft (shown as bend 100 and bend 101), with the two electrodes in the plane of the bends, brings the electrode 102 in contact with the cervix.

FIGS. 11 A through 11C depict an embodiment of a fertility probe of the invention having an electrode-bearing flat at the insertion end of the probe body. The tip of the probe is modified so as to fit more easily into the opening between the cervix and the fornix region and at the same time to make one of the electrodes contact the cervix. The modification is accomplished, in effect, by carving out a portion of the thickness of insertion end 111 to form a flat, retaining electrode 112 on the remaining flat portion of the tip, which now has the shape of a partial cylinder. Electrode 112 is on the inside of the part-cylindrical insertion end 111 and it is this electrode that comes into contact with the cervix. This arrangement of the electrode 112 may be visualized to substitute in FIG. 3B for the electrode 30 shown there.

Figure 11C:
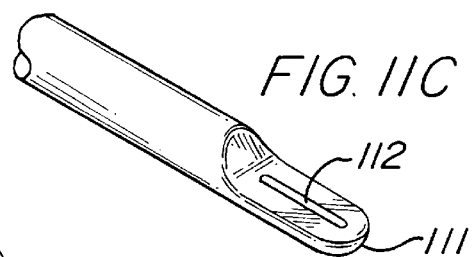
FIGS. 11A through 11C depict an embodiment of a fertility probe of the invention having an electrode-bearing flat at the insertion end of the probe body.
Figure 11A:
Figure 11B:
Figure 12A:
FIGS. 12A through 12C depict an embodiment of a fertility probe of the invention having two electrode-bearing flats at the insertion end of the probe body.
Figure 12B:
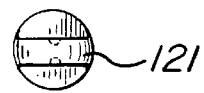
Figure 12C:
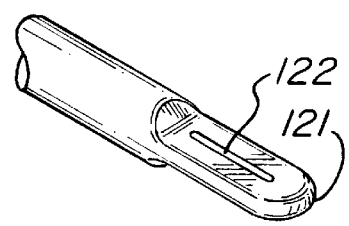

The probe of FIGS. 12A through 12C takes the approach of FIGS. 11A through FIG. 11C a step further. FIGS. 12A through 12C depict an embodiment of a fertility probe of the invention having two electrode-bearing flats at insertion end 121 of the probe body. Both electrodes have been moved closer toward the axis of the probe body due to the carving out of flats on both sides of the tip 121 of the cylindrical probe body.

Figure 13A:
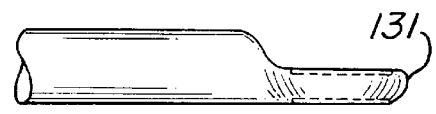
FIGS. 13A through 13C depict an embodiment of a fertility probe of the invention having an electrode-bearing flat at the insertion end of the probe body that extends outwardly beyond the remainder of the probe body.
Figure 13B:
Figure 13C:
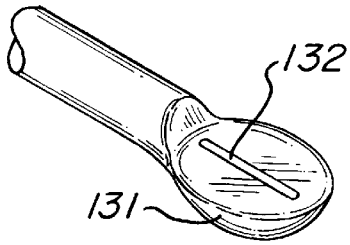

FIGS. 13A through 13C depict an embodiment of a fertility probe of the invention having an electrode-bearing flat portion at the insertion end of the probe body that extends outwardly beyond the diameter of the remainder of the probe body. The added feature here is that the flat portion 131 widens out so as to improve the fit into the posterior fornix region, with the inside electrode 132 making contact with the cervix.

Figure 14A:
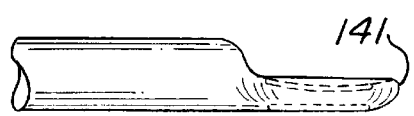

FIGS. 14A through 14C depict an embodiment of a fertility probe of the invention having an electrode-bearing concavity at the insertion end of the probe body that extends outwardly beyond the diameter of the remainder of the probe body. This probe represents yet another improvement of the fit-optimization concept whereby the fit of the probe is further improved by bending the half carved out insertion end 141 in the rough shape of a spoon. The inside electrode 142 makes contact with the cervix.

The probe of FIGS. 15A through 15D takes the approach of FIGS. 11A through 11C a step farther. FIGS. 15A through 15D depict another embodiment of a fertility probe of the invention having an electrode-bearing flat at the insertion end of the probe body that extends outwardly beyond the diameter of the remainder of the probe body. The insertion end 151 has been carved out to introduce a substantially fork-like appearance.

FIGS. 16A through 16C depict an embodiment of a fertility probe of the invention having two elongated protrusions 161 extending from the insertion end of the probe between the electrodes, the axis of elongation corresponding substantially to the axis of said insertion end. The protrusions guide one of electrodes 162 and 163 into contact with the cervix.

FIGS. 17A through 17C depict an embodiment of a fertility probe of the invention having both a bend in the probe body and an electrode-bearing concavity at the insertion end of the probe body. This probe represents another improvement in the optimization of the fit, whereby the concavity 171 is curved up so as to fill the space of the posterior fornix region more effectively. The electrodes 172 and 173 are on the top and bottom sides of the curved scoop, the electrode 172 contacting the cervix.

Although an exemplary embodiment of the invention has been described in detail above, those skilled in the art will readily appreciate that the embodiment may be modified extensively without materially departing from the novel teachings and advantages of the invention. For example, the body of the probe need not be of any particular length or circular in cross-section, but can be of any length sufficient to contact the cervix and of any cross section that fits comfortably within the female vagina of interest. Similarly, the electrodes can be of any shape or size, provided that they are capable of being attached to the insertion end of the body of the probe. All such modifications fall within the scope of this invention as defined in the following claims.

What is claimed is:

1. A probe for monitoring fertility status in a female mammal, said probe comprising:

a. an elongated body having an insertion end, a back end and a central section having a rounded cross-section, b. two electrodes attached to said body at said insertion end, and c. orienting means for orienting the body so that at least one of said electrodes touches the cervix of the female wherein at least one of said electrodes is non-metallic, and wherein said electrodes are attached to said body on opposite sides of said insertion end, and wherein said orienting means comprises at least one concavity at said insertion end, said concavity bearing one of said electrodes.

\* \* \* \* \*